(12) United States Patent
Boyd

(10) Patent No.: US 7,673,500 B2
(45) Date of Patent: Mar. 9, 2010

(54) FLUID MONITORING APPARATUS AND METHOD

(75) Inventor: Nathan Boyd, Manchester (GB)

(73) Assignee: Intelisys Ltd. (GB)

( * ) Notice: Subject to any disclaimer, the term of this patent is extended or adjusted under 35 U.S.C. 154(b) by 670 days.

(21) Appl. No.: 10/595,838

(22) PCT Filed: Nov. 8, 2004

(86) PCT No.: PCT/GB2004/004728

§ 371 (c)(1),
(2), (4) Date: Oct. 24, 2006

(87) PCT Pub. No.: WO2005/052573

PCT Pub. Date: Jun. 9, 2005

(65) Prior Publication Data

US 2007/0163334 A1    Jul. 19, 2007

(30) Foreign Application Priority Data

Nov. 15, 2003    (GB) ................................ 0326659.0

(51) Int. Cl.
*G01N 1/00* (2006.01)
(52) U.S. Cl. ..................................... 73/64.56
(58) Field of Classification Search ................. 73/64.56
See application file for complete search history.

(56) References Cited

U.S. PATENT DOCUMENTS

| 3,492,964 A | | 2/1970 | Martin |
| 3,619,072 A | * | 11/1971 | O'Hara et al. ............... 356/246 |
| 4,163,392 A | * | 8/1979 | Fleenor et al. ........... 73/864.35 |
| 5,400,137 A | | 3/1995 | Winslow et al. |
| 6,021,664 A | | 2/2000 | Granato et al. |
| 2002/0011266 A1 | | 1/2002 | Garver et al. |

FOREIGN PATENT DOCUMENTS

EP    0336794 A    3/1989

* cited by examiner

*Primary Examiner*—Hezron Williams
*Assistant Examiner*—Rodney T Frank
(74) *Attorney, Agent, or Firm*—Adams Intellectual Property Law

(57) ABSTRACT

A fluid monitoring apparatus for monitoring a fluid in a fluid mains supply, the apparatus comprising means for connecting the apparatus to the mains supply, a testing chamber, a fluid tester, testing a variable of a fluid in the testing chamber and a purger for purging a volume of fluid from the testing chamber which volume of fluid is substantially larger than the volume of the testing chamber, thereby replacing the fluid in the testing chamber with a new fluid volume.

19 Claims, 3 Drawing Sheets

FLUID MONITORING APPARATUS AND METHOD

FIELD OF THE INVENTION

This is a national phase application of International Application PCT/GB04/004728, filed Nov. 8, 2004, and claims priority to United Kingdom Patent Application No. 0326659.0, filed Nov. 15, 2003. The present invention relates to fluid monitoring apparatus and particularly, though not exclusively, to mains water monitoring apparatus. The present invention also relates to fluid mains, especially but not exclusively water mains, to which such an apparatus is coupled. The present invention also relates to fluid monitoring methods.

BACKGROUND OF THE INVENTION

Mains water supplies need to be monitored for the well-being of the populous and to assist in the maintenance and upkeep of those supplies. Monitoring of such supplies up to now has been carried out by local inspection. A human operative will visit a mains hydrant, gaining access thereto by a culvert or the like, collect a sample of mains water from the hydrant branch and move on, returning periodically.

This has several disadvantages. It is intensive in terms of skilled manpower requirements and only tests water in the hydrant branch. Further, for many forms of monitoring water needs to removed from the location for testing as a result of which its properties may change.

It is an aim of preferred embodiments of the present invention to obviate or overcome a disadvantage of the prior art, whether such disadvantage or prior art is referred to herein or otherwise.

SUMMARY OF THE INVENTION

According to the present invention in a first aspect, there is provided a fluid monitoring apparatus for monitoring a fluid in a fluid mains supply, the apparatus comprising means for connecting the apparatus to the mains supply, a testing chamber, a fluid tester, testing a variable of a fluid in the testing chamber and a purger for purging a volume of fluid from the testing chamber which volume of fluid is substantially larger than the volume of the testing chamber, thereby replacing the fluid in the testing chamber with a new fluid volume.

Thus fresh fluid can be tested.

Suitably, the apparatus is suitable for coupling to a hydrant connected to the mains supply.

Suitably, the apparatus comprises a purge controller for controlling the purger to determine the volume to be purged. Suitably, the apparatus comprises a pressure sensor for measuring the fluid pressure. Suitably, the purge controller uses the measured pressure to determine the period for which the purger should operate. Suitably, the period is determined by comparing the pressure in a look-up table for a suitable purge time. Suitably, the purge controller comprises a microprocessor.

Suitably, the purger is configured to act for a purge time such that the fluid from the mains supply enters the testing chamber.

Suitably, the fluid tester comprises a turbidity tester. Suitably, the apparatus comprises an electrical conductivity tester. Suitably, the apparatus comprises a temperature tester.

Suitably, the apparatus is configured whereby purged fluid is purged from the apparatus to atmosphere.

Suitably, the apparatus comprises a memory for storing fluid test information. Suitably, the apparatus comprises means to enable data from the memory to be downloaded to an external device.

Suitably, the apparatus comprises a power cell.

Suitably, the fluid comprises a liquid. Suitably, the liquid comprises water.

Suitably, the mains supply is a mains water supply.

According to the present invention in a second aspect, there is provided a fluid mains to which an apparatus according to the first aspect of the present invention is coupled.

Suitably, the fluid mains is a liquid mains.

Suitably, the liquid mains is a water mains.

According to the present invention in a third aspect, there is provided a method of operating a fluid monitoring apparatus for monitoring a fluid in a fluid mains supply, which method comprises the steps of connecting the apparatus to a mains supply, testing a variable of a fluid in a testing chamber and purging a volume of fluid from the testing chamber which volume of fluid is substantially larger than the volume of the testing chamber, thereby replacing the fluid in the testing chamber with a new fluid volume.

BRIEF DESCRIPTION OF THE DRAWINGS

The present invention will now be described, by way of example only, with reference to the drawings that follow; in which.

DESCRIPTION OF THE PREFERRED EMBODIMENTS

Figure 1:
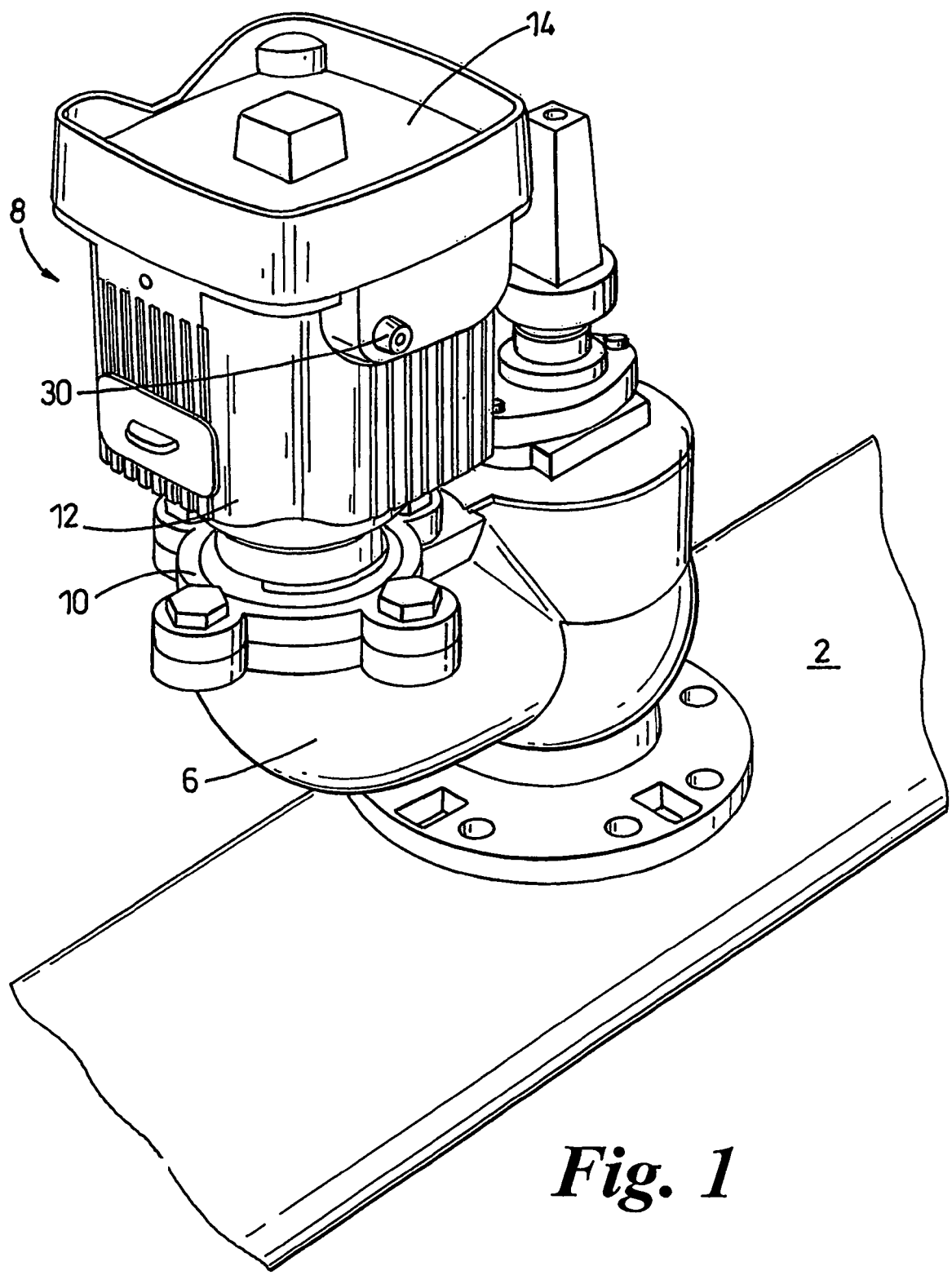
FIG. 1 is a perspective illustration of an apparatus according to the present invention attached to a hydrant.
Figure 2:
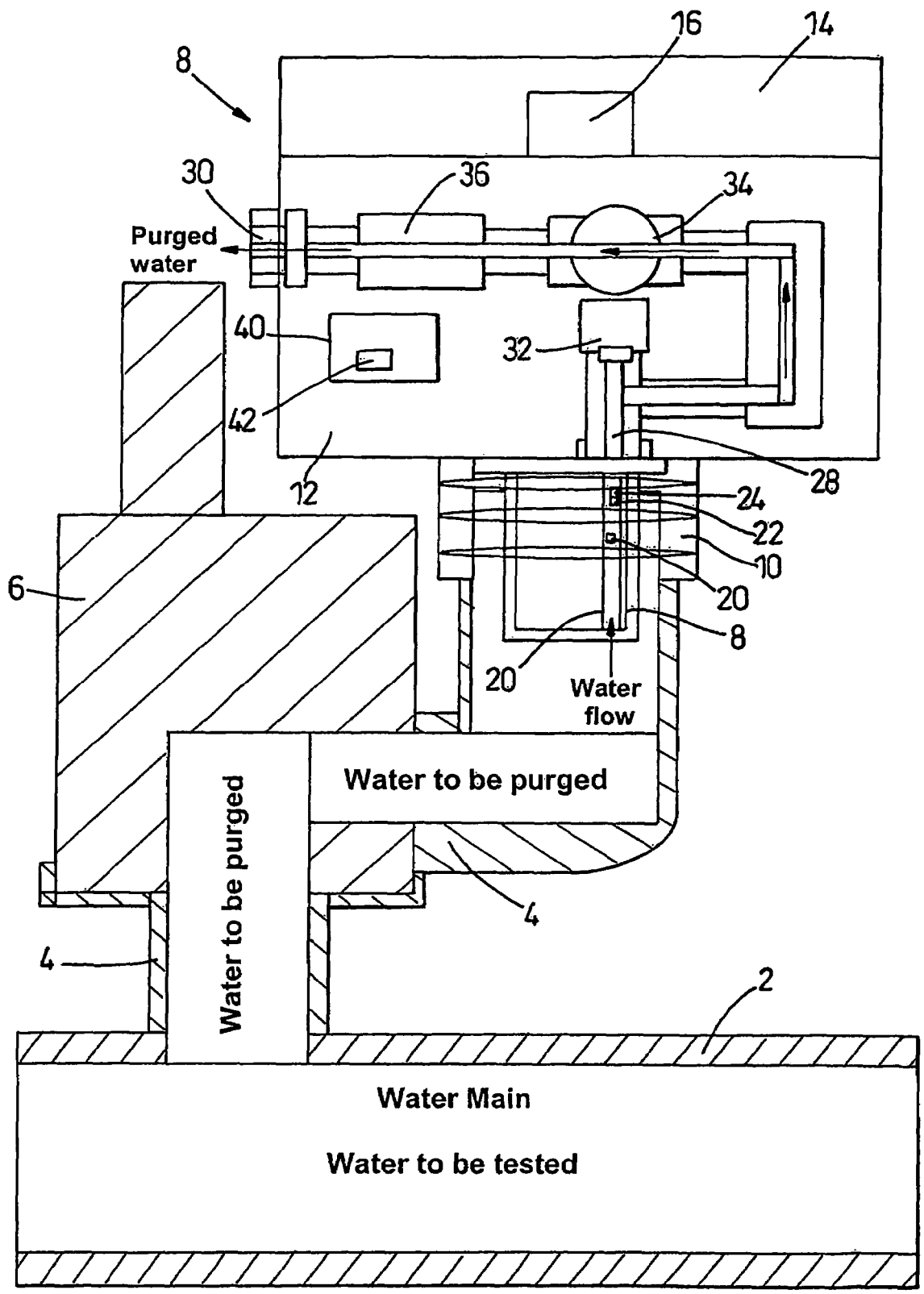
FIG. 2 is a schematic cross sectional elevation of the apparatus shown in FIG. 1.

Referring to FIGS. 1 and 2 of the drawings that follows, there is shown a mains water supply 2 (as an example of a fluid mains) from which extends a hydrant branch 4 to a hydrant 6. The hydrant branch 4 can be up to one meter long in practice (though the present invention is not limited to this or any other length).

Coupled to and mounted on the hydrant 4 is a fluid monitoring apparatus 8 according to a preferred embodiment of the present invention. In this case, the fluid monitoring apparatus is a water monitoring apparatus. The monitoring apparatus 8 is attached to the hydrant stand-pipe screw thread (not shown) by connection means comprising a thread attachment (indicated schematically at 10), which is secured to a case 12 of the apparatus 8 closed with a lid 14. The lid 14 is secured to the case by an attachment nut 16. Extending from the thread attachment and partially into the branch 4 is a sensor head 18 defining therein a testing chamber 20 into which water from the mains 2 flows. For the purpose of the present invention the hydrant branch 4 extends from the mains supply 2 to the entrance to the testing chamber 20.

The sensor head 18 carries turbidity, electrical conductivity and temperature sensors 20, 22, 24 respectively. These are fluid testers.

Figure 3:
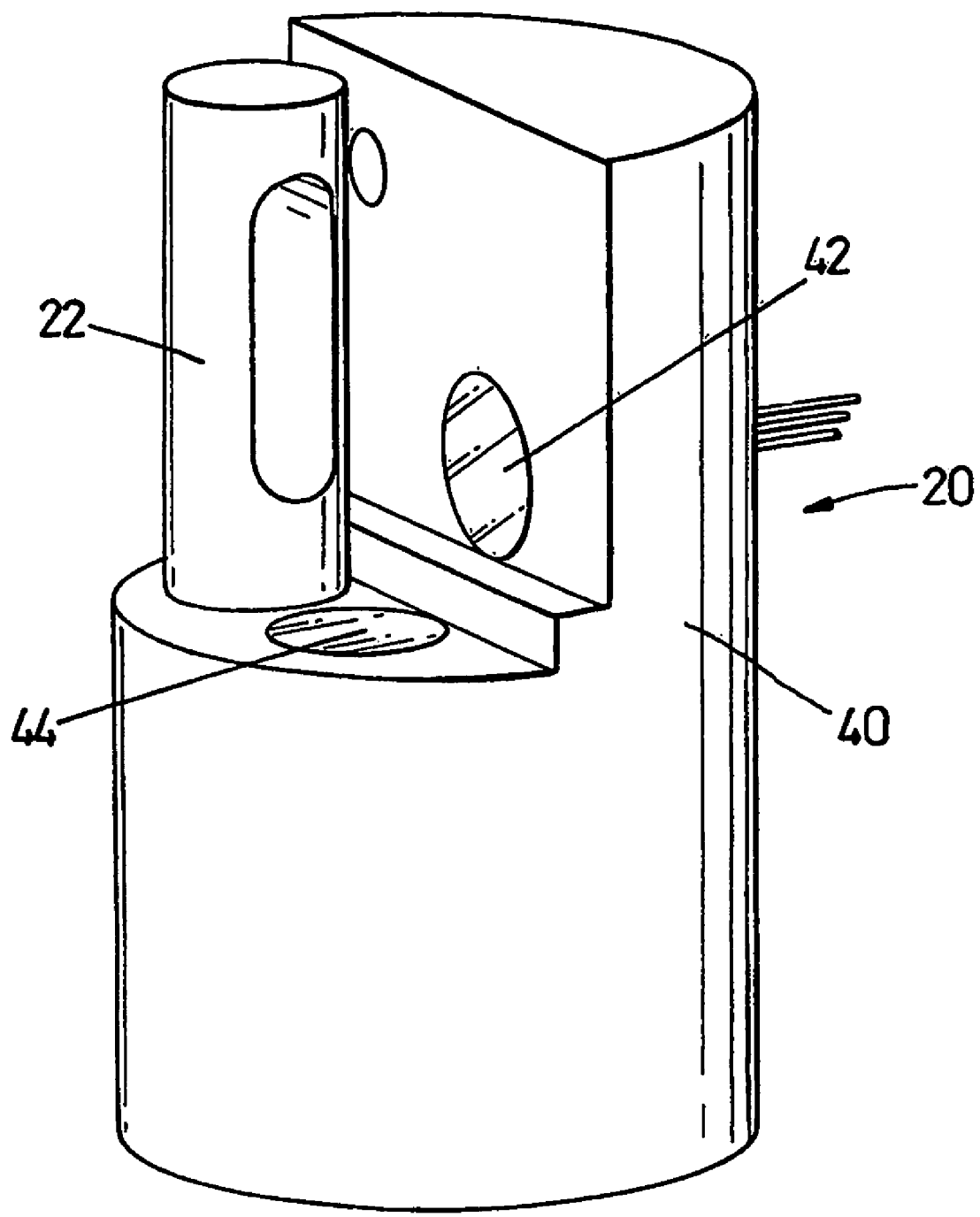
FIG. 3 is a schematic perspective view of a turbidity sensor for use in the apparatus show in the preceding figures.

Referring to FIG. 3 of the drawings that follow, turbidity sensor 20 measures turbidity by using a nephelometric turbidity cell 40, which measures scattered light at 90° to the emitter with the intensity of the reflected light being proportional to the concentration of particles within the sample. An infra-red light emitting diode (not shown) is mounted behind one of the sapphire glass windows 42, 44 and a corresponding detector (not shown) behind the other window 44, 42. This allows, a resolution and accuracy at the lower end of the scale (0-10 Nephelometric Turbidity Unit(NTU)).

Electrical conductivity is measured to indicate the presence or absence of salts, and is often used as a surrogate measure for the dissolved load within a solution. The electrical conductivity sensor 22 (see also FIG. 3) uses four-pole probes giving a linear output allowing for easier calibration. To some extent, such a sensor self-compensates for algal and particle fouling on the plates ensuring a low drift. For instance this can be a K25 sensor from Sentek Ltd, Braintree, Essex, United Kingdom.

The temperature sensor 24 is a high accuracy thermistor encapsulated within the electrical conductivity sensor 20.

From the sensor head 18 a fluid flow path 28 is defined to an outlet 30. In a branch of the main fluid flow path 28 there is located a pressure sensor 32. Part of the flow path is defined by a solenoid valve 34 and another part by a non-return valve 36 before the outlet 30. The outlet 30 opens to atmosphere.

The apparatus further comprises a battery powered cell 38 for powering the apparatus 8.

Also provided is a microprocessor controller 40 and associated memory 42, which controller 40 receives signals from the sensors 20, 22, 24, and controls the solenoid valve 34.

Referring in particular to FIG. 2, it is noted that in the branch 4 and the fluid flow path 28 of the apparatus 8 there is a substantial volume of water. In practice this water may not have the same characteristics as the water in the mains supply.

A mode of operation of this embodiment of the present invention will not be described.

Controller 40 controls the apparatus 8 to sample the water in the mains supply 2 periodically, say daily. Apart from when carrying out fluid monitoring the apparatus 8 is dormant and has no material effect on the mains supply 2. When the controller 40 determines a test is to be carried out to monitor the water it receives a signal from the pressure sensor 32 indicative of the water pressure and from a look-up table stored in memory 42 determines a time for which the solenoid valve 34 needs to be open in order to purge sufficient water through the apparatus 8 so that the water in the sensor head 18 is mains water. Thus the solenoid valve 34 acts as a purger and controller 40 as a purge controller. That is, all of the water from the testing chamber 20 back to the water mains 2 has to be purged. The actual purge time required based on the current pressure can be determined empirically.

The controller 40 then controls the solenoid valve 34 to be opened for the period determined from the look-up table thereby to purge water through the apparatus 8 to atmosphere via the outlet 30. The solenoid valve 34 is then closed and readings are taken of turbidity, electrical conductivity and temperature from the respective sensors 20, 22, 24. These are then stored in the memory 42 associated with the microprocessor controller 40.

To download information from the microprocessor 40, a data outlet (not shown) can be provided or the apparatus can be BLUETOOTH enabled. In either case the data can be collected by an unskilled operative using a Personal Digital Assistant (PDA) or other data logging device. Modem and radio links can also be used.

The apparatus described herein can be used as a fluid testing apparatus, but is of particular benefit for liquids, especially water.

Attention is directed to all papers and documents which are filed concurrently with or previous to this specification in connection with this application and which are open to public inspection with this specification, and the contents of all such papers and documents are incorporated herein by reference.

All of the features disclosed in this specification (including any accompanying claims, abstract and drawings), and/or all of the steps of any method or process so disclosed, may be combined in any combination, except combinations where at least some of such features and/or steps are mutually exclusive.

Each feature disclosed in this specification (including any accompanying claims, abstract and drawings) may be replaced by alternative features serving the same, equivalent or similar purpose, unless expressly stated otherwise. Thus, unless expressly stated otherwise, each feature disclosed is one example only of a generic series of equivalent or similar features.

The invention is not restricted to the details of the foregoing embodiment(s). The invention extends to any novel one, or any novel combination, of the features disclosed in this specification (including any accompanying claims, abstract and drawings), or to any novel one, or any novel combination, of the steps of any method or process so disclosed.

The invention claimed is:

1. A fluid monitoring apparatus for monitoring a fluid in a fluid mains supply, the apparatus comprising means for connecting the apparatus to the mains supply, a testing chamber, a fluid tester for testing a variable of a fluid in the testing chamber and a purger for purging a volume of fluid from the testing chamber which volume of fluid is substantially larger than the volume of the testing chamber, thereby replacing the fluid in the testing chamber with a new fluid volume, in which the apparatus comprises a pressure sensor for measuring the fluid pressure, the apparatus comprises a purge controller for controlling the purger to determine the volume to be purged and the purge controller uses the measured pressure to determine the period for which the purger should operate, wherein the period is determined by comparing the pressure in a look-up table for a suitable purge time.

2. A fluid monitoring apparatus according to claim 1, in which the apparatus is adapted for coupling to a hydrant connected to the mains supply.

3. A fluid monitoring apparatus according to claim 1, in which the purge controller comprises a microprocessor.

4. A fluid monitoring apparatus claim 1, in which the purger is configured to act for a purge time such that the fluid from the mains supply enters the testing chamber.

5. A fluid monitoring apparatus according to claim 1, in which the fluid tester comprises a turbidity tester.

6. A fluid monitoring apparatus according to claim 1, in which the apparatus comprises an electrical conductivity tester.

7. A fluid monitoring apparatus according to claim 1, in which the apparatus comprises a temperature tester.

8. A fluid monitoring apparatus according to claim 1, in which the apparatus is configured whereby purged fluid is purged from the apparatus to atmosphere.

9. A fluid monitoring apparatus according to claim 1, in which the apparatus comprises a memory for storing fluid test information.

10. A fluid monitoring apparatus according to claim 1, in which the apparatus comprises data download means to enable data from the memory to be downloaded to an external device.

11. A fluid monitoring apparatus according to claim 1, in which the apparatus comprises a power cell.

12. A fluid monitoring apparatus according to claim 1, in which the fluid comprises a liquid.

13. A fluid monitoring apparatus according to claim 1, in which the liquid comprises water.

14. A fluid monitoring apparatus according to claim 1, in which the mains supply is a mains water supply.

15. A fluid monitoring apparatus according to claim 1, wherein the fluid monitoring apparatus is coupled to a fluid mains containing a fluid mains supply by the means for connecting the apparatus to the fluid mains supply.

16. A fluid mains according to claim 15, in which the fluid mains is a liquid mains.

17. A fluid mains according to claim 16, in which the liquid mains is a water mains.

18. A method of operating a fluid monitoring apparatus for monitoring a fluid in a fluid mains supply, which method comprises the steps of connecting the apparatus to a mains supply, testing a variable of a fluid in a testing chamber and purging a volume of fluid from the testing chamber which volume of fluid is substantially larger than the volume of the testing chamber, thereby replacing the fluid in the testing chamber with a new fluid volume, in which the fluid pressure is measured by a pressure sensor, a purge controller controls the purger to determine the volume to be purged and the purge controller uses the measured pressure to determine the period for which the purger should operate, wherein the period is determined by comparing the pressure in a look-up table for a suitable purge time.

19. A fluid monitoring apparatus for monitoring a fluid in a fluid mains supply, the apparatus comprising means for connecting the apparatus to the mains supply, a testing chamber, a fluid tester for testing a variable of a fluid in the testing chamber and a purger for purging a volume of fluid from the testing chamber which volume of fluid is substantially larger than the volume of the testing chamber, thereby replacing the fluid in the testing chamber with a new fluid volume, and in which the fluid tester comprises a turbidity tester.

\* \* \* \* \*